(12) United States Patent
Saeidi et al.

(10) Patent No.: US 11,399,720 B2
(45) Date of Patent: *Aug. 2, 2022

(54) CIRCUITS AND METHODS PROVIDING TEMPERATURE MITIGATION FOR COMPUTING DEVICES

(71) Applicant: QUALCOMM INCORPORATED, San Diego, CA (US)

(72) Inventors: Mehdi Saeidi, San Diego, CA (US); Rajat Mittal, Millbrae, CA (US); Melika Roshandell, Carlsbad, CA (US)

(73) Assignee: Qulacomm Incorporated, San Diego, CA (US)

( * ) Notice: Subject to any disclaimer, the term of this patent is extended or adjusted under 35 U.S.C. 154(b) by 1388 days.

This patent is subject to a terminal disclaimer.

(21) Appl. No.: 15/456,779

(22) Filed: Mar. 13, 2017

(65) Prior Publication Data

US 2017/0281010 A1    Oct. 5, 2017

Related U.S. Application Data

(60) Provisional application No. 62/318,418, filed on Apr. 5, 2016.

(51) Int. Cl.
*A61B 5/01*     (2006.01)
*G06F 1/3203*   (2019.01)
(Continued)

(52) U.S. Cl.
CPC ............... *A61B 5/01* (2013.01); *G06F 1/203* (2013.01); *G06F 1/206* (2013.01); *G06F 1/3203* (2013.01);
(Continued)

(58) Field of Classification Search
CPC ........................................ A61B 5/01
(Continued)

(56) References Cited

U.S. PATENT DOCUMENTS 5,940,785 A    8/1999  Georgiou et al.
6,535,798 B1   3/2003  Bhatia et al.
(Continued)

FOREIGN PATENT DOCUMENTS

CN      101351759 A     1/2009
KR      20090077952 A   7/2009
(Continued)

OTHER PUBLICATIONS

International Search Report and Written Opinion—PCT/US2017/022248—ISA/EPO—dated Jun. 2, 2017.

*Primary Examiner* — Md Azad
(74) *Attorney, Agent, or Firm* — Haynes and Boone, LLP (57) ABSTRACT

A method includes: acquiring temperature values from a plurality of temperature sensors spatially distributed within a device; using the temperature values, calculating skin temperature values corresponding to each of the temperature sensors; comparing the skin temperature values to a first temperature threshold; in response to determining that at least one of the skin temperature values exceeds the first temperature threshold, measuring temperature over time; comparing the temperature over time to a second temperature threshold; and in response to determining that the temperature over time exceeds the second temperature threshold, reducing power consumption of the device.

21 Claims, 5 Drawing Sheets

(51) Int. Cl.
  *G06F 1/20* (2006.01)
  *G06F 1/3287* (2019.01)
  *G06F 1/3296* (2019.01)

(52) U.S. Cl.
  CPC .......... *G06F 1/3287* (2013.01); *G06F 1/3296* (2013.01); *Y02D 10/00* (2018.01)

(58) Field of Classification Search
  USPC ........................................................ 700/299
  See application file for complete search history.

(56) References Cited

U.S. PATENT DOCUMENTS

| | | | |
|---|---|---|---|
| 7,062,933 | B2 | 6/2006 | Burns et al. |
| 7,231,531 | B2 | 6/2007 | Cupps et al. |
| 7,460,932 | B2 | 12/2008 | Johns et al. |
| 8,972,759 | B2 | 3/2015 | Doshi et al. |
| 9,047,067 | B2 | 6/2015 | Anderson et al. |
| 9,116,050 | B2 | 8/2015 | Ahuja et al. |
| 9,268,378 | B2 | 2/2016 | Rotem et al. |
| 9,360,907 | B2 | 6/2016 | Doshi et al. |
| 9,582,052 | B2 | 2/2017 | Mittal et al. |
| 9,971,368 | B2 | 5/2018 | Mittal et al. |
| 10,007,310 | B2 | 6/2018 | Saeidi et al. |
| 2003/0110423 | A1 | 6/2003 | Helms et al. |
| 2004/0088593 | A1 | 5/2004 | Park |
| 2004/0148528 | A1 | 7/2004 | Silvester |
| 2004/0215988 | A1 | 10/2004 | Clabes et al. |
| 2006/0161375 | A1 | 7/2006 | Duberstein et al. |
| 2007/0121492 | A1 | 5/2007 | Johns et al. |
| 2007/0156370 | A1 | 7/2007 | White et al. |
| 2007/0260893 | A1 | 11/2007 | Aguilar, Jr. et al. |
| 2008/0036613 | A1 | 2/2008 | Gaskins et al. |
| 2009/0299543 | A1* | 12/2009 | Cox ........................ G06F 1/203 700/299 |
| 2011/0145605 | A1 | 6/2011 | Sur et al. |
| 2011/0301777 | A1* | 12/2011 | Cox ........................ G06F 1/206 700/299 |
| 2011/0301778 | A1 | 12/2011 | Liang et al. |
| 2012/0075992 | A1 | 3/2012 | Shahidi et al. |
| 2012/0096288 | A1 | 4/2012 | Bates et al. |
| 2013/0193776 | A1 | 8/2013 | Tanaka |
| 2013/0321041 | A1 | 12/2013 | Kim et al. |
| 2014/0358318 | A1 | 12/2014 | Lin et al. |
| 2015/0006937 | A1* | 1/2015 | Rotem ..................... G06F 1/206 713/324 |
| 2015/0148981 | A1* | 5/2015 | Kong ................. G05D 23/1917 700/299 |
| 2018/0073933 | A1 | 3/2018 | Keskin et al. |
| 2018/0085070 | A1* | 3/2018 | Chen ..................... A61B 5/0008 |
| 2018/0143862 | A1 | 5/2018 | Saeidi et al. |

FOREIGN PATENT DOCUMENTS

| | | |
|---|---|---|
| KR | 20090119745 A | 11/2009 |
| KR | 20120063340 A | 6/2012 |
| WO | WO-2012145214 A1 | 10/2012 |

\* cited by examiner

CIRCUITS AND METHODS PROVIDING TEMPERATURE MITIGATION FOR COMPUTING DEVICES

CROSS-REFERENCE TO RELATED APPLICATION

The present application claims the benefit of U.S. Provisional Patent Application No. 62/318,418, filed Apr. 5, 2016, and entitled "Circuits and Methods Providing Temperature Mitigation for Computing Devices," the disclosure of which is incorporated by reference herein in its entirety.

FIELD OF THE DISCLOSURE

Embodiments of present disclosure generally relate to temperature mitigation in computing devices and, more particularly, to temperature mitigation systems that use a calculated skin temperature as a basis for thermal mitigation.

BACKGROUND

A conventional modern smart phone may include a system on chip ("SOC"), which has a processor and other operational circuits. Specifically, an SOC in a smart phone may include a processor chip within a package, where the package is mounted on a printed circuit board ("PCB") internally to the phone. The phone includes an external housing and a display, such as a liquid crystal display ("LCD"). A human user, when using the phone, physically touches the external housing and the display.

As the SOC operates, it generates heat. In one example, the SOC within a smart phone may reach temperatures of 80° C.-100° C. Furthermore, conventional smart phones do not include fans to dissipate heat. During use, such as when a human user is watching a video on a smart phone, the SOC generates heat, and the heat is spread through the internal portions of the phone to the outside surface of the phone.

The outside surface of the phone is sometimes referred to as the "skin." The outside surface includes the part of the external housing that is physically on the outside of the phone as well as any other externally-exposed portions, such as an LCD display. It is generally accepted that the skin of the phone should not reach temperatures higher than about 40° C.-45° C. due to safety and ergonomic reasons. As noted above, the SOC within the smart phone may reach temperatures of 80° C.-100° C., although the temperature of the SOC is not felt directly at the skin of the phone. Instead, heat dissipation within the phone often means the skin temperature of the phone is at a lower temperature than the SOC temperature. Furthermore, whereas changes to SOC temperature may be relatively quick (e.g., seconds), changes to device skin temperature may be relatively slow (e.g., tens of seconds or minutes).

Conventional smart phones include algorithms to control the skin temperature by reducing a frequency of operation of the SOC when a temperature sensor on the SOC reaches a threshold level. However, SOC temperature can be a poor proxy for device skin temperature.

SUMMARY

To provide temperature mitigation in computing devices, illustrative methods and systems of the present disclosure are directed to a thermal mitigation system which calculates skin temperature at a multitude of locations and uses the skin temperature values in a thermal mitigation algorithm.

According to one method, temperature values are acquired from a plurality of temperature sensors spatially distributed within a device. Using the temperature values, skin temperature values corresponding to each of the temperature sensors are calculated. The skin temperature values are compared to a first temperature threshold and, in response to determining that skin temperature values exceed the first temperature threshold, the temperature over time is measured. The temperature over time is then compared to a second temperature threshold and, in response to determining the temperature over time exceeds the second temperature threshold, the power consumption of the device is reduced.

According to one embodiment, a computing device includes a computer processor and a plurality of temperature sensors disposed within a physical housing of the computing device. The temperature sensors are in communication with the computer processor which is configured to calculate a skin temperature value for each of the respective temperature sensors and based at least in part on data from the respective temperature sensors. In response to determining at least one of the skin temperature values exceeds a first temperature threshold, the computer processor calculates a temperature over time value from temperature data from at least one of the temperature sensors. The computer processor then compares the temperature over time value to a second temperature threshold and, in response to determining the temperature over time value exceeds the second temperature threshold, reduces an operating parameter of the computer processor.

According to another embodiment, a computing device includes a means for generating temperature information at a plurality of locations within the computing device. The computing device also includes a means for calculating a skin temperature value for each of the respective temperature information generating means. The computing device includes a means for calculating a cumulative temperature over time value in response to determining that at least one of the skin temperature values exceeds a first temperature threshold. The computing device further includes a means for reducing an operating parameter of at least one processing core of a system on chip in response to determining that the cumulative temperature over time value exceeds a second temperature threshold.

In addition, yet another embodiment provides a non-transitory computer readable medium having computer-readable instructions stored thereon, wherein the computer-readable instructions when executed by a processing unit cause the processing unit to acquire temperature values from a plurality of temperature sensors spatially distributed within a device; using the temperature values, calculate skin temperature values corresponding to each of the temperature sensors; compare the skin temperature values to a first temperature threshold; in response to determining that at least one of the skin temperature values exceeds the first temperature threshold, measure temperature over time; compare the temperature over time to a second temperature threshold; and in response to determining that the temperature over time exceeds the second temperature threshold, reduce power consumption of the device.

These and other advantages of the present disclosure will be apparent to those ordinarily skilled in the art having the benefit of this disclosure.

DESCRIPTION OF ILLUSTRATIVE EMBODIMENTS

Illustrative embodiments and related methods of the present disclosure are described below as they might be employed in a system to calculate skin temperatures used as a basis for thermal mitigation. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, illustrative embodiments of the present disclosure are directed to systems to calculate skin temperature values that correspond to a plurality of temperature sensors and apply the calculated skin temperature values to perform thermal mitigation. In a generalized embodiment of the present disclosure, a computer processor includes a number of integrated circuit chips (e.g., a SOC that has a number of processing cores, a power management integrated circuit ("PMIC"), and the like). The chips are disposed within a computing device, such as a smart phone. The smart phone also includes a battery, a printed circuit board hosting the chips, a touchscreen display, and an outer housing, among other things. The power supply, e.g., a PMIC, converts the voltage and current from the battery into a voltage and current that can be used by the other chips. As the chips operate, they produce heat.

The heat from the chips spreads throughout the phone according to the heat conduction properties of the physical materials that make up the phone. However, it is generally expected that the skin of the phone will not be as hot as the chips, at least under usual operating conditions. The system includes one or more processes that monitor temperature sensors within the chips and on the printed circuit board and calculate values for skin temperature at various spatially separated points on the skin.

A process, either hardware-based or software-based or a combination thereof, uses the skin temperature readings for thermal mitigation. Specifically, in this generalized example, the process compares the skin temperature readings to a first temperature threshold to determine whether any of the skin temperature readings go above a first threshold. If the skin temperature readings are below the first threshold, then the process keeps monitoring the temperatures without providing thermal mitigation action. If, however, one or more of the skin temperature readings is above the first threshold, the process moves to another action that includes measuring a cumulative temperature over time. If the cumulative temperature over time crosses a second threshold (e.g., the temperature readings during a 2 minute interval exceed the second threshold), then the process begins thermal mitigation by, e.g., reducing a clock frequency of the processor or some other operating parameter. In this case, the second temperature threshold may be referred to as a second cumulative temperature threshold. If the cumulative temperature over time does not cross the second threshold, then the process continues to monitor the one or more skin temperature readings above the first threshold over time until the skin temperature readings drop below the first threshold.

The processes described herein may be embodied as computer-readable instructions that are read from a tangible non-transitory machine-readable medium and executed by the processor, in some instances, as part of an operating system kernel running on the processor. In another generalized embodiment, the process may be embodied as a hardware process built in to the processor. However, in many embodiments, thermal changes at the skin of the device and at the integrated circuit chips change on the order of seconds or minutes, so that software is generally fast-acting enough.

Figure 1:
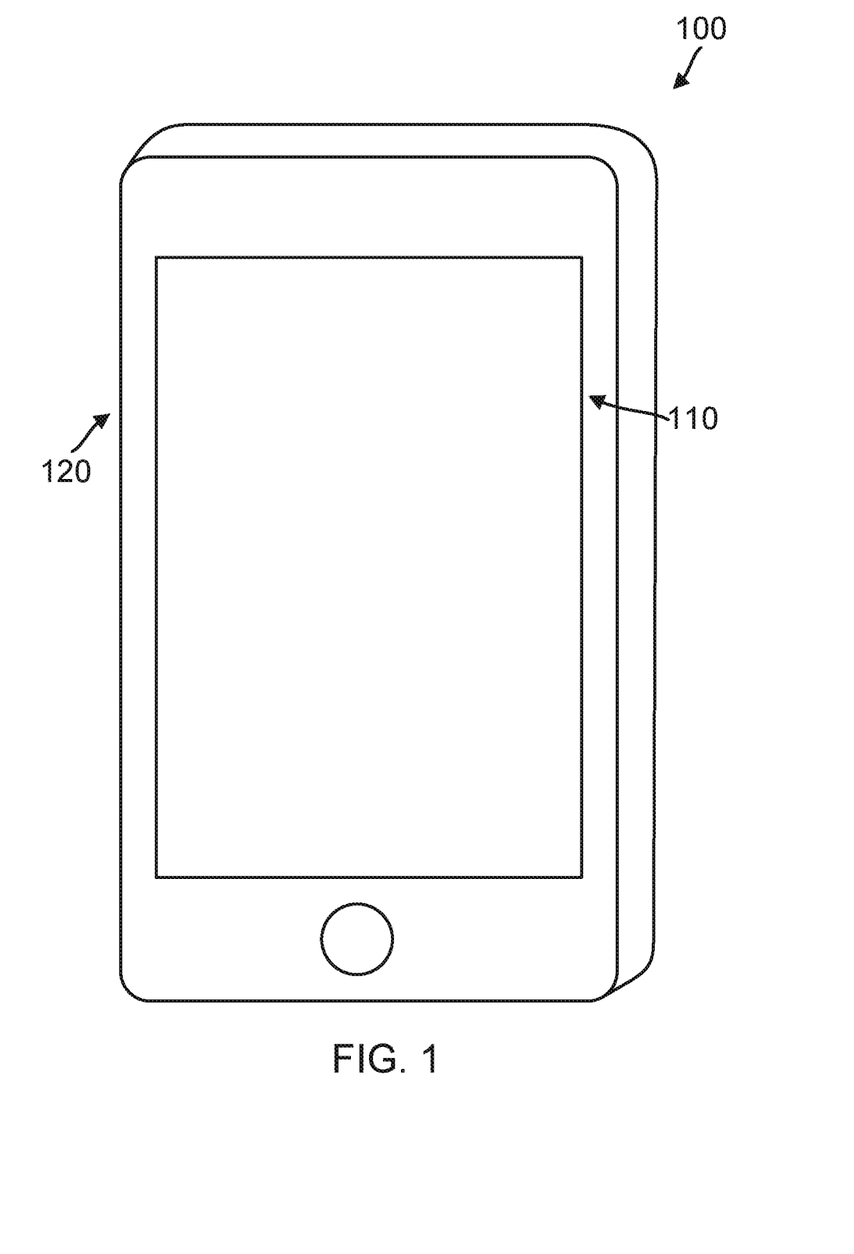
FIG. 1 is a simplified diagram illustrating a computing device 100 in which various embodiments of the present disclosure may be implemented.

FIG. 1 is a simplified diagram illustrating an example computing device 100 in which various embodiments of the present disclosure may be implemented. In the example of FIG. 1, computing device 100 is shown as a smart phone. However, the scope of embodiments is not limited to a smart phone, as other embodiments may include a tablet computer, a laptop computer, or other appropriate device. In fact, the scope of embodiments includes any particular computing device, whether mobile or not. Embodiments including battery-powered devices, such as tablet computers and smart phones may benefit from the concepts disclosed herein. Specifically, the concepts described herein provide techniques to reduce heat that is dissipated outside of computing device 100, thereby providing comfort for a human user and conserving battery power.

As shown in FIG. 1, computing device 100 includes an outer surface or skin 120, which may be expected to come into contact with hands or other parts of the body of a human user. The outside surface 120 includes, e.g., metal surfaces, plastic surfaces, and the surfaces that make up display unit 110. In one example, display unit 110 is a capacitive LCD touchscreen, so that the surface of display unit 110 is either glass or plastic-coated glass. The outside surface 120 therefore includes the various external surfaces, such as, for example, the display unit 110 and the other parts of the external housing. Although not shown in the vantage point of FIG. 1, the back side of computing device 100 includes another part of the outer surface of the device, and specifically another part of the exterior housing, which may be arranged in a plane parallel to a plane of display unit 110.

FIG. 1 does not show a computer processor, but it is understood that a computer processor is included within computing device 100. In one example, the computer processor is implemented in a SOC within a package, and the package is mounted to a printed circuit board and disposed within the physical housing. In conventional smart phones, the package including the processor is mounted in a plane parallel to a plane of the display surface and a plane of the back surface.

As the computer processor and other chips operate, they produce heat, which dissipates throughout the physical structure of computing device 100. Depending on the specific thermal properties of computing device 100, heat from the operation of the chips may reach uncomfortable or near-uncomfortable temperatures on the outside surface 120 of computing device 100. The illustrative computer processor within computing device 100 provides functionality to control the heat felt on the outside surface of the computing device 100 by calculating a skin temperature and adjusting a frequency, voltage or other operating parameter of the processor if appropriate. Various illustrative embodiments described herein provide one or more advantages over conventional solutions. For instance, some embodiments use a technique to calculate skin temperature that avoids the use of real-time power consumption measurements, as explained more fully below.

Figure 2:
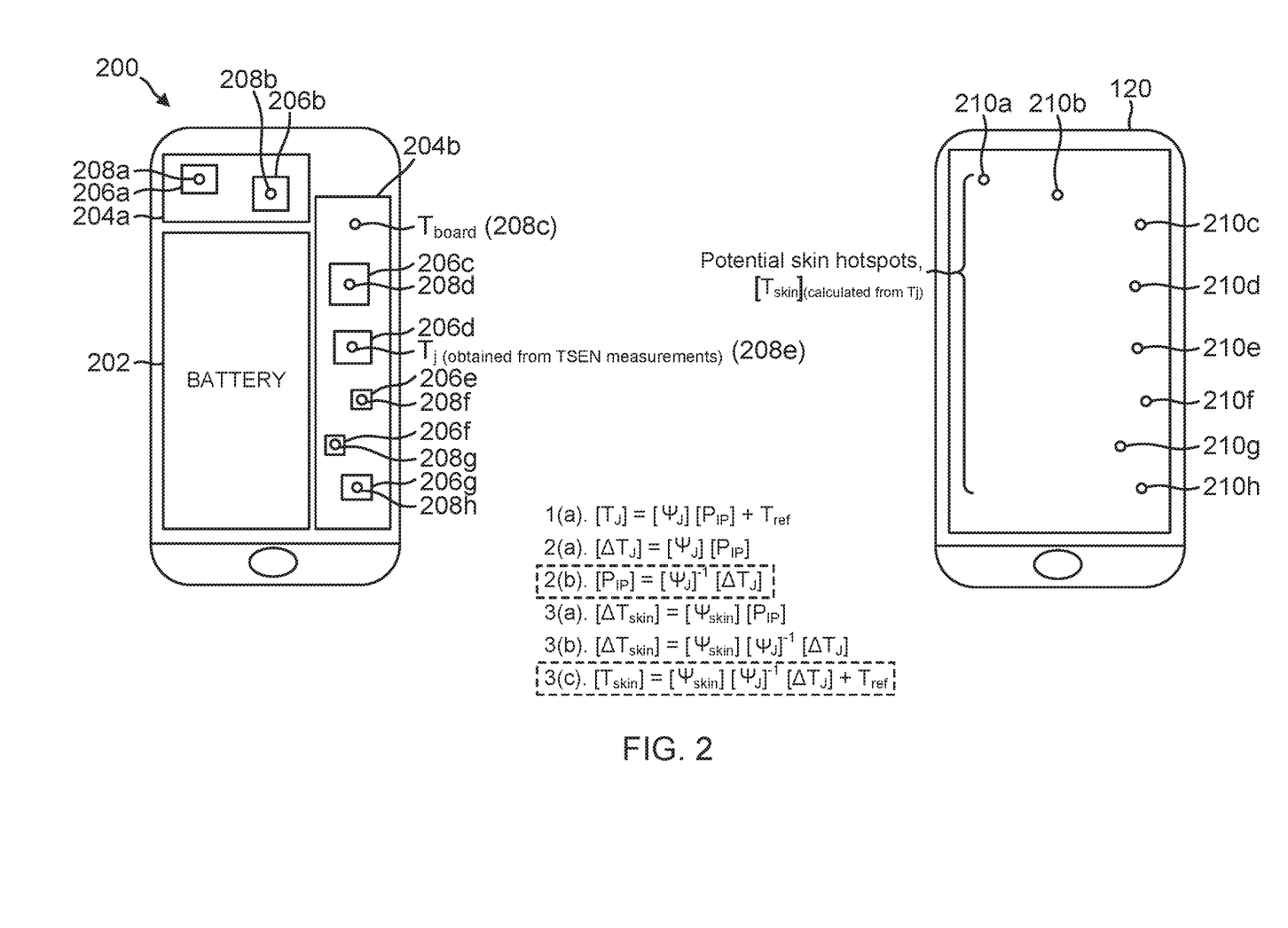
FIG. 2 is an example diagram of the illustrative computing device 100 showing the inner hardware architecture 200 and outside surface 120 of the computing device 100.

FIG. 2 is an example diagram of the computing device 100 of FIG. 1. On the left side is an example of the architecture of the inner hardware 200 of the computing device 100, and on the right side is an example illustration of an outside surface 120 of the computing device 100.

Referring to inner hardware architecture 200, computing device 100 includes a battery 202, two printed circuit boards 204a and 204b, multiple integrated circuit chips 206a-g, and temperature sensors ("TSENS") 208a-h on printed circuit board 204b and in integrated circuit chips 206a-g. As will be explained in more detail below, each sensor 208a-h may represent a single sensor or multiple sensors. Battery 202 and integrated circuit chips 206a-g are disposed within computing device 100 so that they are enclosed within the physical housing of the computing device 100 as indicated by exterior surface 120. Battery 202 and integrated circuit chips 206a-g, as well as printed circuit boards 204a and 204b are also in thermal contact with the physical housing so that the heat generated by battery 202 and integrated circuit chips 206a-g is conducted to the exterior surface 120 of device 100.

In the context of an illustrative integrated circuit chip (or PCB), there may be multiple temperature sensors within that one integrated circuit chip (or PCB). In such illustrative embodiments, a junction temperature ("$T_J$") refers to a temperature sensor detecting a highest temperature out of a group of temperature sensors within a given integrated circuit chip (or PCB). As mentioned above, each sensor 208a-h may represent a single sensor or multiple sensors. Thus, over time, a junction temperature for a given integrated circuit chip (or PCB) may correspond to different temperature sensors within that integrated circuit chip (or PCB).

Looking at the right hand drawing of exterior surface 120, there are multiple dots on outer surface 120 of the computing device 100. Each of the dots represents a potential skin hotspot 210a-h ($T_{skin}$) that spatially corresponds to one of temperature sensors 208a-h of the left-hand side drawing.

FIG. 2 also includes multiple equations 1(a)-3(c), which illustrate techniques to calculate skin temperature at the potential skin hotspots 210a-h. Equation 1(a) includes a matrix $[T_J]$, which is a single column matrix, where each of the entries in the matrix corresponds to one of the junction temperatures $T_J$ at temperature sensors 208a-h. Note that each temperature sensor 208a-h may have a junction temperature $T_J$, as the location of $T_J$ in architecture 200 is illustrative in nature. Furthermore, $[T_J]$ may be populated by temperature readings from each of the sensors, regardless which of the sensors may sense a highest temperature at a particular time. The matrix $[\Psi_J]$ is a square matrix having as many rows and columns as there are junction temperatures $T_J$. Each of the entries in the matrix $[\Psi_J]$ represents a measure of thermal resistance. Considering one of the junction temperatures, one of the rows of the matrix $[\Psi_J]$ corresponds to a given temperature sensor 208a-h.

It is understood that for each integrated circuit chips 206a-g, the temperature at the respective integrated circuit chip is dependent on heat produced by the integrated circuit chip itself, as well as by heat produced by neighboring integrated circuit chips. Therefore in a given row, one of the entries is an indication of thermal resistance between that integrated circuit chip and its respective temperature sensor (self-heating), and the other entries each indicate a thermal resistance between one of the other integrated circuit chips and the respective temperature sensor (mutual heating between integrated circuit chips).

The matrix $[P_{IP}]$ is a single column matrix that indicates power consumption at each of temperature sensors 208a-h, keeping in mind that temperature sensor 208c on printed circuit board 204b may have zero power consumption. $T_{ref}$ is an indication of a reference temperature, such as, for example, at exterior surface 120 or an assumed temperature for ambient atmosphere or a user's skin. Equations 2(a) and 2(b) indicate that power use/consumption over time affects temperature changes at each temperature sensor 208a-h.

The matrix $[\Psi_{skin}]$ is another matrix having measurements of thermal resistance. The matrix $[\Psi_{skin}]$ is a square matrix with as many rows and columns as there are potential skin hotspots 210a-n. Each row corresponds to a potential skin hotspot 210a-n, with each of the entries in a row providing an indication of thermal resistance between that particular potential skin hotspot and one of temperature sensors 208a-n. Equation 3(a) indicates that changes of power consumption at integrated circuit chips 206a-g causes temperature changes at each of the potential skin hotspots 210a-g.

The matrix $[T_{skin}]$ is a single column matrix, where each of the entries corresponds to a calculated skin temperature value at a respective one of the potential skin hotspots 210a-h. Equation 3(c) can be derived from the previous equations, and it indicates that, in certain illustrative methods, the calculation of skin temperature at each of the potential skin hotspots 210a-h can be achieved without having to use a real-time measurement of power consumption at integrated circuits 206a-g. In this example, a real-time measurement would not be necessary since $\Delta T_J$ represents a change in junction temperature over time. This is advantageous in some illustrative embodiments, considering that a real-time measurement of power consumption may not be available in many computing devices.

Various embodiments and related methods of the present disclosure include using one or more of the equations of FIG. 2 to calculate skin temperature for each of the potential skin hotspots 210a-h. It should be noted that, in certain illustrative methods, the matrices $[\Delta T_J]$, $[\Psi_J]$, and $[\Psi_{skin}]$ may be pre-calculated based on testing or simulation so that they are not calculated in real time. For instance, the thermal resistance values of $[\Psi_J]$ may be device-dependent and further may be determined from simulation or testing. Also, $[\Delta_J]$ may be calculated by simulation or testing by measuring power consumption ($[P_{IP}]$) and using equation 2(a) after $[\Psi_J]$ is known. Additionally, $[\Psi_{skin}]$ by measuring power consumption ($[P_{IP}]$) and changes in skin temperature and using either equation 3(a) or 3(b). In any event, the matrices $[\Delta T_J]$, $[\Psi_J]$, and $[\Psi_{skin}]$ may be calculated at any appropriate time (e.g., after manufacture but before shipping of a device) and stored to the nonvolatile memory of the device. A computer processor of the device may then access those matrices from memory during normal operation in order to perform the actions described at FIGS. 4 and 5.

Figure 3:
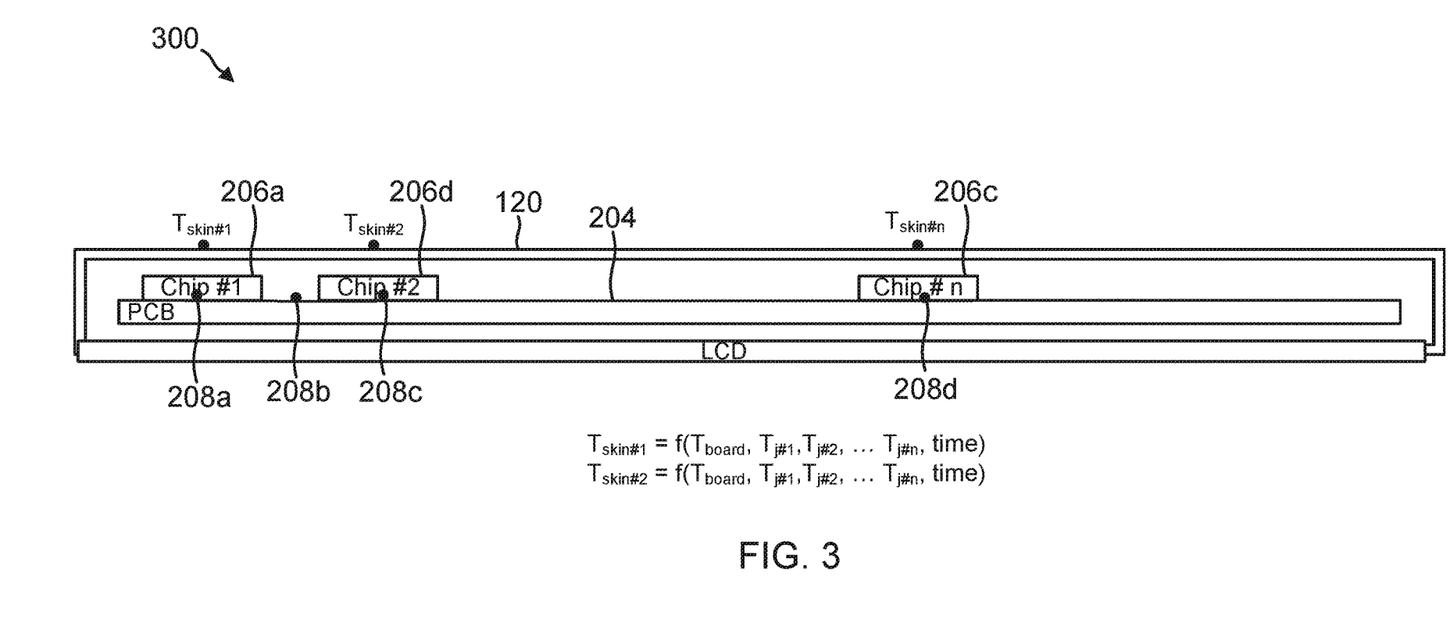
FIG. 3 shows a side-on view of an illustrative computing device 300, such as computing device 100 of FIG. 1 or 2.

FIG. 3 shows a side-on view of an example computing device 300, such as computing device 100 FIG. 1 or 2. In FIG. 3, the potential skin hotspots $T_{skin}$ are shown as $T_{skin\ \#1}$, $T_{skin\_\#2}$, and $T_{skin\_\#3}$ spatially located along exterior or outside surface 120. Here, temperature sensors 208a-d are located at integrated circuit chip 206a, printed circuit board 204, integrated circuit chip 206b, and integrated circuit chip 206c, which in turn provide a plurality of temperature readings. Although FIG. 3 only shows three integrated circuit chips 206a-c, the number of temperature sensors and integrated circuit chips may be scaled as appropriate.

FIG. 3 also includes two equations generalizing an example function to calculate skin temperature at the first two potential skin hotspots. As shown, $T_{skin\_\#1}$ may be calculated as a function of the board temperature $T_{board}$ received from sensor 208b, temperature $T_{j\_\#1}$ received from sensor 208a, temperature $T_{j\_\#2}$ received from sensor 208c, and temperature $T_{j\_\#n}$ received from sensor 208d, as well as the time period over which a given temperature is maintained. Likewise, $T_{skin\_\#2}$ may be calculated as a function of the board temperature $T_{board}$ received from sensor 208b, temperature $T_{j\_\#1}$ received from sensor 208a, temperature $T_{j\_\#2}$ received from sensor 208c, and temperature $T_{j\_\#n}$ received from sensor 208d, as well as the time period over which a given temperature is maintained.

Figure 4:
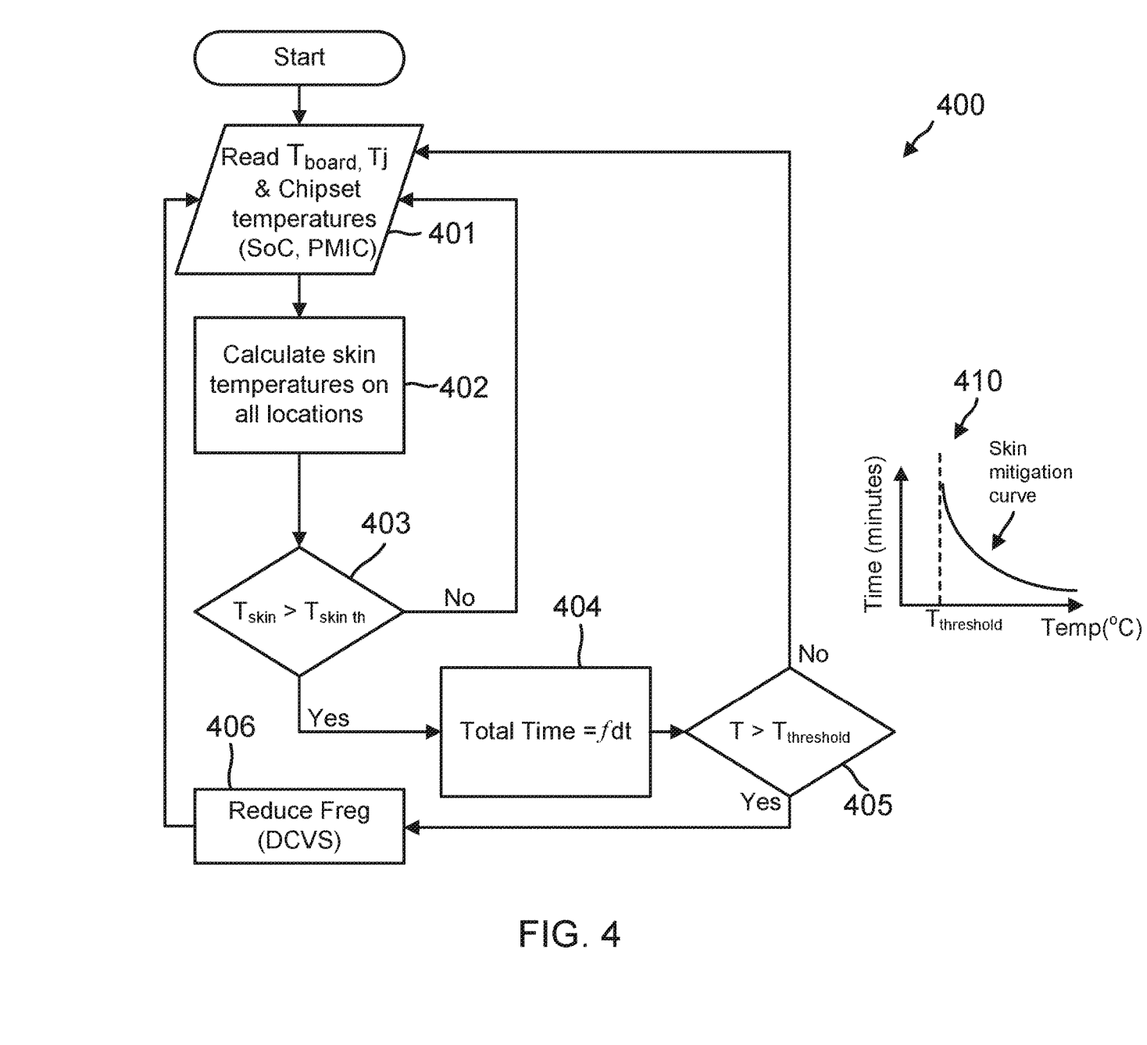
FIGS. 4 and 5 are flow diagrams of processes for providing thermal mitigation, according to certain illustrative methods of the present disclosure.

A flow diagram of an example method 400 of providing thermal mitigation is illustrated in FIG. 4. In one example, method 400 is performed by a thermal mitigation unit, which may include hardware and/or software functionality at a processor of computing device 100. In some examples, a thermal mitigation unit includes processing circuitry that executes computer readable instructions to calculate skin temperature values and to perform a temperature mitigation function according to a particular algorithm. As the device operates during normal use, the thermal mitigation unit performs the actions of method 400. Therefore, as a human user leaves the device idle, makes phone calls, sends text messages, watches videos, and the like, the thermal mitigation unit may continually perform the actions of method 400 to ensure that the device skin temperature does not reach a pre-defined uncomfortable level.

At action 401, the thermal mitigation unit reads temperature sensing data TSENS from temperature sensors 208a-h at integrated circuit chips 206a-g and on printed circuit board 204b. Examples are shown above at FIG. 2, where dot 208c on printed circuit board 204b indicates a temperature sensor (or multiple sensors) on the printed circuit board, and the dots 208 a,b,d,e,f,g,h in integrated circuit chips 206a-h indicate temperature sensors that provide a junction temperature $T_J$ for a respective integrated circuit chip. Thus, in certain embodiments, the temperature sensors may be deemed a means for generating temperature information at a plurality of locations within the computing device.

At action 402, the thermal mitigation unit calculates skin temperatures 210a-h for each of the different locations, such as corresponding to each of the different integrated circuit chips 206a-h and temperature sensor 208c located on printed circuit board 204b. Note that the temperature sensors 208 may be located anywhere within architecture 200, as architecture 200 is illustrative in nature only. The equations of FIG. 2 provide techniques that may be used by the thermal mitigation unit to calculate the skin temperature values, as previously described. Thus, in certain embodiments, one or more processors of the thermal mitigation unit may be deemed a means for calculating skin temperatures.

At action 403, the thermal mitigation unit compares each of the calculated skin temperatures $T_{skin}$ against a temperature threshold, $T_{skin\_th}$. The value of the temperature threshold may be any appropriate amount, and it represents a temperature level that may be expected to begin an undesirable rise in device skin temperature. In certain illustrative embodiments, the value of the temperature threshold will depend on the heat conduction properties of the particular device. For instance, a device with a heat spreading layer built into it may be assigned a higher temperature threshold than a device that allows a more rapid heat transfer from the SOC to the skin. In some scenarios, the temperature threshold may be assigned to a device based upon experimentation and/or known heat transfer properties of the design. As noted above, $T_{skin\_th}$ may be saved to memory in the processor of computing device 100 and accessed by a thermal mitigation unit as it performs method 400. Thus, in certain embodiments, one or more processors of the thermal mitigation unit may be deemed a means for comparing the skin temperature values to a first temperature threshold.

If the measured temperature reading is not greater than the temperature threshold $T_{skin\_th}$, then the thermal mitigation unit continues to calculate and monitor skin temperature values. However, if one or more of the calculated skin temperature values is greater than the temperature threshold $T_{skin\_th}$, the thermal mitigation unit moves to action 404. At action 404, the thermal mitigation process then measures temperature over time, which may be accomplished in a variety of ways. Thus, in certain embodiments, one or more processors of the thermal mitigation unit may be deemed a means for measuring the temperature over time. An example includes integrating a temperature reading (one of the junction temperatures) from at least one of the temperature sensors over a particular time period. Another example is a cumulative, moving window average of temperature over time. An example is shown in the skin mitigation curve 410. For instance, cumulative temperature over time at action 404 may represent an area that may be compared to the area under skin mitigation curve 410. The curve 410 may indicate a cumulative temperature over time reading above which mitigation may be performed.

At action 405, the thermal mitigation process determines whether the temperature over the time period is greater than a second threshold ($T_{threshold}$), where, in this example, the second threshold corresponds to cumulative temperature over time expected to cause an undesirably high device skin temperature (e.g., 43° C.). Nevertheless, the second threshold is specific to a particular device design, and may be assigned to a particular device through experimentation and/or known heat transfer properties of the design. In the particular example of FIG. 4, the energy threshold corresponds to the boundary of curve 410. Thus, in certain embodiments, one or more processors of the thermal mitigation unit may be deemed a means for determining whether the temperature over time is greater than a second temperature threshold.

If the temperature over the time period is less than the second threshold $T_{threshold}$, then the thermal mitigation unit continues to monitor the temperature. However, if the temperature over time is greater than the second energy threshold $T_{threshold}$, then the thermal mitigation unit moves to action 406. At action 406, the thermal mitigation unit reduces the energy consumed by at least one of the integrated circuit chips or other system components. Thus, in certain embodiments, one or more processors of the thermal mitigation unit may be deemed a means for reducing an operating parameter when the temperature over time exceeds the second energy threshold. In one example, the thermal mitigation unit reduces an operating frequency of one or more integrated circuit chips, thereby reducing power consumption. However, the scope of embodiments may include any appropriate thermal mitigation technique, such as putting cores or other components in an idle state. In fact, reduction of any operating parameter, such as frequency or voltage, is within the scope of embodiments. The process continues to iteratively repeat as the computing device operates, continually calculating skin temperature and taking appropriate mitigation steps according to the algorithm.

Various embodiments may include one or more advantages over conventional techniques. For instance, various embodiments calculate multiple skin temperature values, each of the different skin temperature values corresponding to a different physical location on the physical housing of the device. In other words, various embodiments may take into account real-world performance of the computing device, which may result in hot spots at one or more of the physical locations of the housing. Therefore, such systems may allow for thermal mitigation in response to determining that any one or more of the physical locations may experience excessive heat absent intervention. By contrast, some conventional systems may simply compare a temperature reading on a chip directly to a threshold, but as explained above, a chip temperature may be a poor proxy for skin temperature.

Furthermore, various embodiments may take into account mutual heating and self-heating among the components inside the device. For instance, mutual heating and self-heating may be determined using simulation or testing of a manufactured device, and such phenomena may be affected by the different materials that are used within a particular device. Taking into account mutual heating and self-heating may provide for skin temperature estimations that are more indicative of actual skin temperature during normal operation of the device.

Moreover, various embodiments may use a first threshold (e.g., at action 403) before beginning to calculate a cumulative temperature over time. And then, such embodiments may mitigate temperature after exceeding a second threshold corresponding to cumulative temperature over time. Such embodiments may delay mitigation for as long as is desirable or practical, thereby maintaining a high level of performance and user experience before frequency throttling or voltage reduction takes place. Nevertheless, such embodiments may be expected to provide appropriate thermal mitigation at times that would be expected to benefit from thermal mitigation and according to one or more of the equations discussed with respect to FIG. 2.

Figure 5:
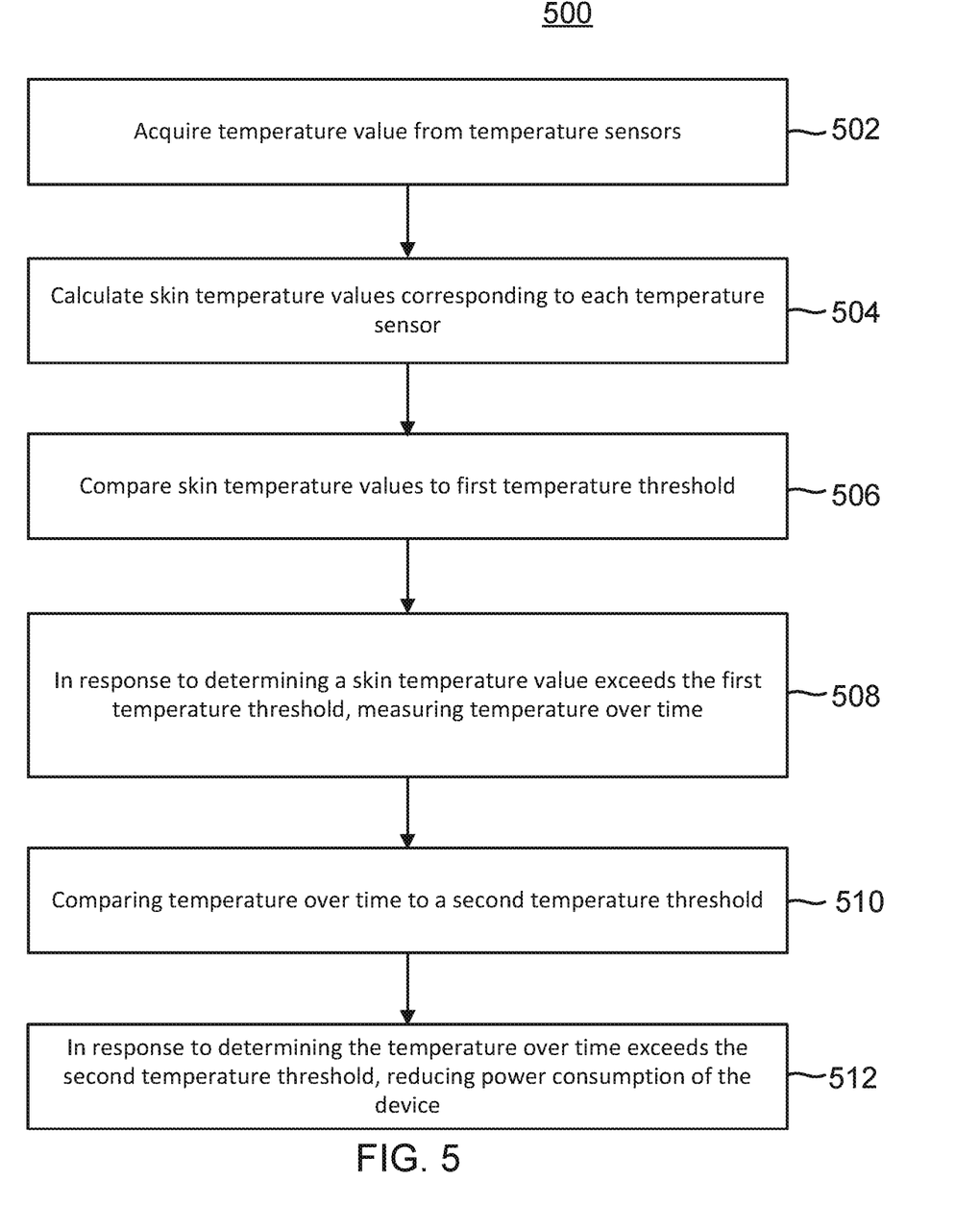

FIG. 5 is a flow chart of another method 500, according to certain illustrative embodiments of the present disclosure. At action 502, temperature values are acquired from a plurality of temperature sensors spatially distributed within a computing device. At action 504, skin temperature values corresponding to each of the temperature sensors are calculated using the acquired temperature values. At action 506, the skin temperature values are compared to a first temperature threshold. At action 508, in response to determining that at least one of the calculated skin temperature values exceeds the first temperature threshold, the temperature of the sensors are measured over time. At action 510, the temperature over time is compared to a second temperature threshold. At action 512, in response to determining that the temperature over time exceeds the second temperature threshold, the power consumption of the device is reduced. The aforementioned actions may be performed by a thermal mitigation unit comprising hardware and/or software as previously described herein.

The scope of the illustrative embodiments are not limited to the specific methods shown in FIG. 4 or 5. Other embodiments may add, omit, rearrange, or modify one or more actions. For instance, methods 400 or 500 may also include functionality to return the clock frequency to a previous level or otherwise to increase the clock frequency when thermal mitigation is no longer desired, such as after determining that skin temperature has decreased.

Although various embodiments and methods have been shown and described, the disclosure is not limited to such embodiments and methods and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A method, comprising:
    acquiring temperature values from a plurality of temperature sensors spatially distributed within a device;
    using the temperature values, calculating skin temperature values corresponding to each of the temperature sensors;
    comparing the skin temperature values to a first temperature threshold;
    in response to determining that at least one of the skin temperature values exceeds the first temperature threshold, measuring cumulative temperature over time, wherein measuring the cumulative temperature over time includes integrating temperature values from at least one of the temperature sensors over time;
    comparing the cumulative temperature over time to a second temperature threshold; and
    in response to determining that the cumulative temperature over time exceeds the second temperature threshold, reducing power consumption of the device.

2. The method of claim 1, wherein acquiring the temperature values comprises acquiring temperature values from at least one of the temperature sensors positioned on a circuit board and at least one of the temperature sensors disposed on an integrated circuit chip located within the device.

3. The method of claim 1, wherein calculating the skin temperature values comprises taking into account self-heating at each of the temperature sensors.

4. The method of claim 1, wherein calculating the skin temperature values comprises taking into account mutual heating at each of the temperature sensors.

5. The method of claim 1, wherein reducing the power consumption comprises reducing an operating parameter of the device.

6. The method of claim 1, wherein reducing the power consumption comprises putting one or more cores of the device in an idle state.

7. A computing device comprising:
    a computer processor; and
    a plurality of temperature sensors disposed within a physical housing of the computing device and in communication with the computer processor, the computer processor configured to perform the following operations:
        calculate a plurality of skin temperature values, each of the skin temperature values corresponding to a respective temperature sensor and based at least in part on data from the respective temperature sensors;
        in response to determining that at least one of the skin temperature values exceeds a first temperature threshold, calculate a cumulative temperature over time value from temperature data from at least one of the temperature sensors, wherein calculating the cumulative temperature over time value comprises integrating the temperature data over time;

compare the cumulative temperature over time value to a second temperature threshold; and in response to determining that the cumulative temperature over time value exceeds the second temperature threshold, reduce an operating parameter of the computer processor.

8. The computing device of claim 7, wherein at least one of the temperature sensors is positioned on a circuit board and at least another one of the temperature sensors is disposed within the computer processor.

9. The computing device of claim 7, wherein calculating the skin temperature values comprises taking into account self-heating at the temperature sensors.

10. The computing device of claim 7, wherein calculating the skin temperature values comprises taking into account mutual heating at the temperature sensors.

11. The computing device of claim 7, wherein reducing the operating parameter comprises reducing an operating frequency of the computer processor.

12. The computing device of claim 7, wherein reducing the operating parameter comprises placing one or more cores of the computer processor in an idle state.

13. The computing device of claim 7, wherein each of the skin temperature values corresponds to a physical location on a physical housing of the computing device, the computer processor and the plurality of temperature sensors being disposed within the physical housing.

14. A computing device, comprising:
means for generating temperature information at a plurality of locations within the computing device; and
a processor configured to implement:
means for calculating a plurality of skin temperature values, each of the skin temperature values corresponding to a respective temperature information generating means;
means for calculating a cumulative temperature over time value in response to determining that at least one of the skin temperature values exceeds a first temperature threshold, wherein calculating the cumulative temperature over time value includes integrating temperature information, from at least one of the means for generating temperature information, over time; and
means for reducing an operating parameter of at least one processing core of a system on chip in response to determining that the cumulative temperature over time value exceeds a second temperature threshold.

15. The computing device of claim 14, wherein the means for generating temperature information comprises a plurality of temperature sensors.

16. The computing device of claim 14, wherein:
the means for calculating the skin temperature values and the means for calculating the cumulative temperature over time value comprises a computer processor; and
the means for reducing the operating parameter comprises an operating system kernel running on the computer processor.

17. The computing device of claim 14, wherein the means for calculating the skin temperature values includes means to account for self-heating at each of a plurality of temperature sensors and mutual heating at each of the temperature sensors.

18. The computing device of claim 14, wherein the means for reducing the operating parameter includes means to reduce a clock frequency and voltage of the at least one processing core.

19. A non-transitory computer readable medium having computer-readable instructions stored thereon, wherein the computer-readable instructions when executed by a processing unit cause the processing unit to:
acquire temperature values from a plurality of temperature sensors spatially distributed within a device;
using the temperature values, calculate skin temperature values corresponding to each of the temperature sensors;
compare the skin temperature values to a first temperature threshold;
in response to determining that at least one of the skin temperature values exceeds the first temperature threshold, measure cumulative temperature over time, wherein measuring the cumulative temperature over time includes integrating at least one of the temperature values over time;
compare the cumulative temperature over time to a second temperature threshold; and
in response to determining that the cumulative temperature over time exceeds the second temperature threshold, reduce power consumption of the device.

20. The non-transitory computer readable medium of claim 19, wherein acquiring temperature values includes acquires temperature values from at least one of the temperature sensors positioned on a circuit board and at least one of the temperature sensors disposed on an integrated circuit chip located within the device.

21. The non-transitory computer readable medium of claim 19, wherein calculating skin temperature values takes into account self-heating and mutual heating at each of the temperature sensors.

* * * * *